US009757226B2

(12) United States Patent
Goldberg et al.

(10) Patent No.: US 9,757,226 B2
(45) Date of Patent: *Sep. 12, 2017

(54) CORNEAL IMPLANT AND METHOD OF DELIVERING A CORNEAL IMPLANT

(71) Applicant: ENDOSHIELD, LLC, Key Biscayne, FL (US)

(72) Inventors: Jeffrey L. Goldberg, San Diego, CA (US); Jean-Marie Parel, Miami, FL (US); Francisco Fantes, Key Biscayne, FL (US)

(73) Assignee: ENDOSHIELD, LLC, Key Biscayne, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/062,781

(22) Filed: Mar. 7, 2016

(65) Prior Publication Data

US 2016/0184086 A1 Jun. 30, 2016

Related U.S. Application Data

(63) Continuation of application No. 14/352,503, filed as application No. PCT/US2012/060349 on Oct. 16, 2012, now Pat. No. 9,308,083.

(Continued)

(51) Int. Cl.
*A61F 2/14* (2006.01)
*A61F 9/008* (2006.01)
*A61F 2/16* (2006.01)

(52) U.S. Cl.
CPC ............ *A61F 2/1451* (2015.04); *A61F 2/142* (2013.01); *A61F 2/145* (2013.01); *A61F 2/1453* (2015.04);

(Continued)

(58) Field of Classification Search
CPC ........ A61F 2/142; A61F 2/145; A61F 2/1451; A61F 2/1453

(Continued)

(56) References Cited

U.S. PATENT DOCUMENTS 2,952,023 A   9/1960 Rosen
4,612,012 A   9/1986 White (Continued)

FOREIGN PATENT DOCUMENTS

EP    2067453 A1   6/2009
GB    810232 A     3/1959

(Continued)

OTHER PUBLICATIONS

Written Opinion mailed Jan. 18, 2013 issued in connection with corresponding International Application No. PCT/US12/60349 (6 pages total).

(Continued)

*Primary Examiner* — David H Willse
*Assistant Examiner* — Javier Blanco
(74) *Attorney, Agent, or Firm* — Mark D. Wieczorek; Stuart H. Mayer; Mayer & Williams PC

(57) ABSTRACT

A method of inserting and securing a corneal implant in engaging and fluid-flow limiting relation to the posterior cornea, such as to treat edema. The method includes securing a corneal implant in fluid flow limiting relation to the posterior cornea through an incision in the eye and securing it in place by a variety of steps such as corneal insertion or laser bonding, and preferably by inserting a removable corneal implant including a central region and a plurality of retention member(s) disposed on the periphery thereof into the eye so as to releaseably and removably engage a portion of the eye and thereby retain the corneal implant in abutting and engaging relation with the posterior cornea. The reten- (Continued)

tion members of the corneal implant may also comprise haptic leg(s) extending from the central region.

6 Claims, 8 Drawing Sheets

Related U.S. Application Data

(60) Provisional application No. 61/550,087, filed on Oct. 21, 2011.

(52) U.S. Cl.
CPC ...... *A61F 9/00821* (2013.01); *A61F 9/00834* (2013.01); *A61F 9/00836* (2013.01); *A61F 2002/1683* (2013.01); *A61F 2009/00872* (2013.01)

(58) Field of Classification Search
USPC .................................. 623/5.14, 5.15, 5.11
See application file for complete search history.

(56) References Cited

U.S. PATENT DOCUMENTS

| | | |
|---|---|---|
| 4,693,715 A | 9/1987 | Abel, Jr. |
| 4,772,283 A | 9/1988 | White |
| 6,106,552 A | 8/2000 | Lacombe et al. |
| 6,254,637 B1 | 7/2001 | Lee |
| 7,175,661 B1 | 2/2007 | Chung |
| 2003/0033014 A1 | 2/2003 | Gwon |
| 2004/0243159 A1 | 12/2004 | Shiuey |
| 2005/0177231 A1 | 8/2005 | Ricci et al. |
| 2008/0050423 A1 | 2/2008 | Hsiue |
| 2010/0069915 A1 | 3/2010 | Shiuey |
| 2010/0185281 A1 | 7/2010 | Daphna |

FOREIGN PATENT DOCUMENTS

| | | |
|---|---|---|
| WO | 2008/150319 A1 | 12/2008 |
| WO | 2013/066615 A1 | 5/2013 |

OTHER PUBLICATIONS

International Search Report mailed Jan. 18, 2013 issued in connection with corresponding International Application No. PCT/US12/60349 (2 pages total).

International Preliminary Report on Patentability issued Apr. 22, 2014 in connection with corresponding International Application No. PCT/US12/60349 (7 pages total).

Extended Search Report issued May 19, 2015 issued in connection with corresponding European Patent Application No. 12 845 328.9 (7 pages total).

CORNEAL IMPLANT AND METHOD OF DELIVERING A CORNEAL IMPLANT

CROSS REFERENCE TO RELATED APPLICATIONS

This application is a continuation of U.S. Ser. No. 14/352,503, filed Apr. 17, 2014, entitled, "CORNEAL IMPLANT AND METHOD OF DELIVERING A CORNEAL IMPLANT" which is a 371 of International Application No. PCT/US2012/060349, filed Oct. 16, 2012, entitled "A CORNEAL IMPLANT AND METHOD OF DELIVERING A CORNEAL IMPLANT" which claims benefit and priority to U.S. provisional patent application having Ser. No. 61/550,087 filed on Oct. 21, 2011, entitled "CORNEAL IMPLANT AND METHOD OF DELIVERING A CORNEAL IMPLANT" which are all incorporated herein by reference in their entirety.

FIELD OF THE INVENTION

The present invention relates to corneal implants and to a method of delivering and securing corneal implants in fluid-flow limiting relation to the posterior cornea, such as to treat corneal edema, including removably securing the corneal implant.

DESCRIPTION OF THE RELATED ART

Excess corneal fluid, also known as corneal edema, is a painful condition caused by an accumulation of fluid within the cornea that can lead to loss of corneal clarity and visual acuity. Corneal edema is most often the result of a decreased number or decreased function of the corneal endothelial cells that form a monolayer lining the inside, or posterior, side of the cornea. For example, the endothelial cells can fail to adequately pump aqueous fluid that diffuses into the cornea from the anterior chamber out of the cornea and back into the anterior chamber.

Current treatment for corneal edema includes medical treatment and therapy to dehydrate the cornea with hypertonic saline, and in some cases, corneal transplant. There are approximately 50,000 corneal transplants performed each year in the United States, with similar statistics for Europe. The three major indications for corneal transplant are Fuchs' dystrophy, pseudophakicbullous edema, and corneal transplant rejection. Corneal transplants in the United States and abroad are limited, however, by tissue accessibility, surgical cost, long patient recovery time, changes in refraction affecting vision, availability of corneal specialists, and the risk of transplant rejection or failure, which can be in the range of 10-30%.

Corneal implants have been developed to treat edema while attempting to avoid some of the problems of transplant surgery. For instance, synthetic corneal implants can be used in place of tissue, thereby obviating issues of tissue availability and limiting the possibility of host rejection. However, there are still no acceptable ways of inserting and securing the corneal implants to the eye of a patient that will minimize interference with visual acuity and damage to the eye. For example, some known methods involve suturing the implant to the cornea, or applying a bonding agent to permanently bond the implant to the cornea. However, suturing the implant creates scar tissue, which can interfere with vision, and may be rejected by the patient's body.

Bonding agents may cause chemical damage to the cornea or implant over time, and also may affect vision. Moreover, known corneal implants and methods only permit permanent attachment of the corneal implant, and may even preclude future corneal transplants.

Accordingly, it would be beneficial to have a method of inserting and securing a corneal implant to the cornea that does not interfere with vision, and possibly could even correct vision simultaneously with treating corneal edema. In addition, it would also be beneficial to have a method of inserting a corneal implant such that it can later be removed if necessary, such as for a replacement or if the patient's condition subsides.

SUMMARY OF THE INVENTION

The present invention is directed to a method of delivering and maintain a corneal implant in proximity to the posterior cornea of a patient, as well as to a preferred removable corneal implant. The method and corneal implant are directed to protecting the cornea from excess fluid, such as from the anterior chamber of the eye, thereby keeping the cornea dehydrated. In this manner, the present invention can be used to treat corneal edema, or excess corneal fluid. Further, the method achieves removable retention of the corneal implant in abutting engagement with the posterior cornea such that the corneal implant can be removed at a later time if necessary. This is a significant advance over existing corneal implant and transplant methods which permanently secure the corneal implant to the eye and do not allow the implant to be removed, and in some cases even preclude future corneal transplants. Moreover, the corneal implant of the present invention may be configured to correct vision upon implantation, including myopia, hyperopia, and bifocal correction, in addition to treating corneal edema.

More in particular, in a first preferred embodiment of the present method, a corneal implant including one or more retention members is utilized, the retention members engaging portions of the eye to removably secure the corneal implant in a fluid flow limiting position relative to the posterior cornea. Particularly, the method can comprise an initial step of creating an incision in the eye of a patient needing the corneal implant, such as in proximity to the cornea, and then inserting through the incision a corneal implant having a central region and at least one retention member extending from the periphery of the central region. To facilitate entry, the corneal implant may be temporarily compressed or folded for insertion through an incision of a smaller dimension than the diameter of the corneal implant, although it is understood that a sufficiently large incision can be made to accommodate an unfolded corneal implant. Once inserted, the corneal implant is positioned in engaging and fluid-flow limiting relation to the posterior cornea and secured in place by engaging a portion of the eye with the retention members. Because the retention members can later be removed from that engagement, the retention members are able to removably retain the corneal implant against posterior cornea.

For example, in one embodiment the retention member(s) comprise a hook or claw-type configuration which may be pressed into the posterior cornea to secure the corneal implant in position. Furthermore, the retention member(s) may comprise at least one haptic leg secured to and extending from the central region of the corneal implant, such that when positioned, the distal end of the haptic leg(s) contacts the iris and/or iridocorneal angle and biases the central region of the corneal implant against the posterior cornea, thus maintaining an optimal close, fluid flow limiting contact.

In another embodiment, the method of inserting a corneal implant includes inserting the implant, with or without retention members, into the corneal stroma in or near the posterior cornea. Specifically, the method comprises creating an incision in the eye, such as in the cornea or near to the cornea, and inserting the implant through the incision and into the corneal stroma in fluid-flow limiting relation to the posterior cornea, such as anterior to the Descemet's membrane. In some cases this method may further involve excising a portion of the eye in proximity to the posterior cornea from the corneal stromal side, such as from the sclera or directly in the cornea, thereby creating a corneal pocket. For example, this may entail excising a portion of deep cornea, creating a deep laminectomy corneal pocket. This pocket is then extended into the corneal stroma, preferably the posterior corneal stroma just anterior to Descemet's membrane, forming a deep corneal pocket. Once formed, the corneal implant is inserted through the incision, through the pocket, and positioned within the corneal pocket in engaging and fluid-flow limiting relation to the posterior cornea, such as adjacent and anterior to the Descemet's membrane. The incision is then closed leaving the corneal implant in its proper location.

In still another possible embodiment of the present method, a laser is used to bond the corneal implant in position relative to the posterior cornea. Specifically, the method in this embodiment comprises creating the incision in the eye of the patient needing the corneal implant, again preferably in proximity to the cornea. A corneal implant is then inserted through the incision and positioned in engaging, fluid-flow limiting relation to the posterior cornea. With the implant positioned, a laser is applied at a plurality of locations along the perimeter of the corneal implant, and may be applied continuously along the perimeter and/or along substantially the entire perimeter of the corneal implant. The laser application is maintained until the corneal implant is bonded with the posterior cornea. It is understood that if desired a corneal implant with one or more retention members may also be used.

In addition to the aforementioned method, the present invention is also directed to an improved corneal implant, preferably, but not necessarily configured for use with one of the preceding methods. In this regard, the corneal implant can preferably include a central region made of a biocompatible polymer material, such as a hydrophobic material, which is transparent to allow for visibility therethrough. The central region also preferably has an index of refraction high enough to permit refractive vision correction if needed. Preferably, the central region of the implant has an arcuate configuration that corresponds with and matches the curvature of the posterior cornea. This shape promotes effective placement of the corneal implant in abutting engagement with the posterior cornea upon implantation in a manner that resists fluid flow.

The corneal implant further includes at least one, but preferably a plurality of retention members secured to and extending away from a periphery of the central region. These retention members, which can be integral with the central region, each have a contact point disposed distally from the central region of the implant and in contacting relation with the eye upon implantation. Preferably, these contact points removably engage the eye in a manner that urges and retains the central region of the corneal implant in position relative to the posterior cornea. To achieve effective positioning, the retention members can include clasps, hooks, or other similar structures that are structured to engage a portion of the eye, such as the posterior cornea or other nearby ocular structure, to secure the corneal implant in position while permitting later disengagement of the eye and removal if necessary.

In some embodiments, the retention members comprise at least one, but ideally two to four haptic legs each having a contact point disposed distally from the central region to engage a portion of the iris and/or iridocorneal angle. The haptic leg(s) further have a biasing configuration which may be hinged to bias the central region of the corneal implant against the posterior cornea, such as by applying pressure to the central region upon implantation, when they are in position to effectively push off against the portion of the eye to which they are engaged. Moreover, the corneal implant may include only haptic leg(s), only other types of retention member(s), or any combination thereof.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
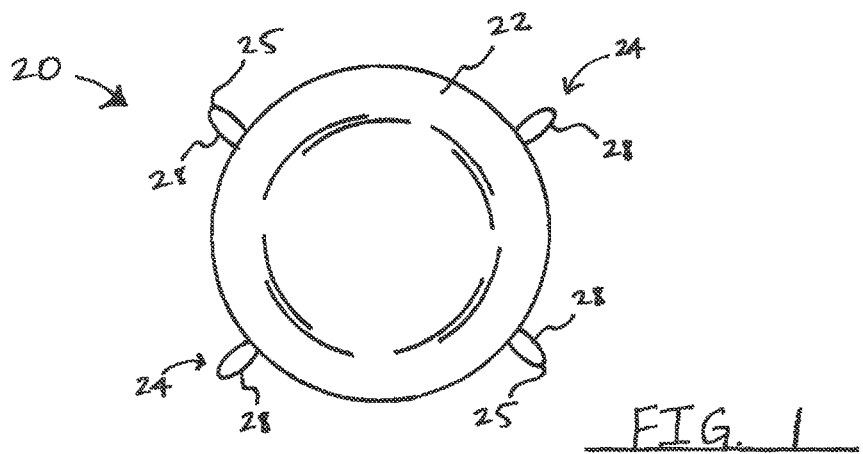
FIG. 1 is a planar view of the posterior side of the corneal implant of the present invention.

The present invention is directed to a method of delivering and securing a corneal implant to the posterior cornea of a patient, preferably in a removable manner, as well as to a corneal implant that can preferably be implemented with that method. The method can be used to insert corneal transplants, such as from a live or recently deceased donor, although preferably, and as will be described in greater detail, it is preferably used for the introduction of corneal implants made of natural or synthetic material. It is noted that for purposes of clarity the subsequent description of the present method may be described using the preferred corneal implant, however, such use of the preferred corneal implant in said description is not intended to be limiting or to necessarily require use of the preferred corneal implant. More in particular, this preferred corneal implant can be made of a medical-grade biocompatible material, such as a polymer, which is biologically inert so as not to interfere with the patient's biochemistry. For example, the corneal implants inserted by the present method can be made of acrylic polymers and its co-polymers, styrene polymers and its co-polymers, siloxane polymers, including silicone rubber and its co-polymers, natural and synthetic collagen and its co-polymers, fluoroethylene and its co-polymers. Moreover, the corneal implant may have a sufficiently high refractive index to permit vision correction of the recipient upon implantation. Accordingly, the present method can be utilized to treat corneal edema and other corneal disorders, as well as to provide refractive correction, independent of tissue donors and the problems attendant to using living tissue, such as waiting for an appropriate donor, matching the blood type, antigens, and other factors between the donor and recipient, screening for diseases in the donor tissue, possible host rejection, post-operative infections, etc.

As previously noted, the methods of inserting a corneal implant, to be described, are preferably, but not necessarily, achieved using the preferred embodiment of the corneal implant with certain optimal characteristics and structure. Before discussing the specific embodiments of the present method, however, the preferred corneal implant 20 is described. Specifically, this preferred corneal implant 20, includes a central region 22 which is preferably generally round, and is at least partially transparent so as not to interfere with the vision of the patient. Further, the central region 22 preferably measures approximately 3-10 millimeters in diameter, although it may optimally be 5 6 millimeters in diameter in certain embodiments. At least the central region 22 is preferably made of a biocompatible polymer material, such as described previously, which is biologically inert and of medical grade quality. For example, the central region 22, can be formed of hydrophobic materials such as acrylic, poly(methyl methacrylate) (PMMA), poly(styrene-block-isobutylene-block-styrene) (SIBS), silicone rubber such as polydimethylsiloxane (PDMS), chlorotrifluoroethylene (CTFE). Alternately, however, it may be made of a hydrophilic material, examples of which include poly(2-hydroxyethyl methacrylate-co-methylmethacrylate) (pHEMA-MMA) and poly(2-hydroxyethyl methacrylate-co-ethylmethacrylate) (pHEMA-EMA), having a water content in the range of about 10-50%, or natural or synthetic collagen. Accordingly, the central region 22 is structured and positioned to inhibit the flow of excess corneal fluid when oriented pursuant to the present method.

Furthermore, many of these materials are at least semi-rigid, and as such it may be preferred that the hardness or stiffness of the central region 22 be approximately equivalent to the rigidity of the cornea. For instance, the hardness or stiffness of the central region 22 may be approximately 10 MPa, although greater degrees of rigidity are contemplated. Conversely, however, these same materials are also still somewhat flexible, thus making the central region 22 at least temporarily foldable so as to reduce a dimension thereof for implantation of the corneal implant 20 in the described method.

It is also noted that the central region 22 is configured to correspond to the contour of the posterior cornea. As seen in FIGS. 1-3, the central region 22 has an arcuate, or curved, configuration providing an anterior surface 26 disposable toward the front of the eye on implantation, and a posterior surface 27 disposable in facing relation to the interior of the eye upon implantation. The anterior surface or curvature 26 is structured to correspondingly match a curvature of the posterior cornea, as seen in FIG. 3, which shows the corneal implant 20 in position relative to the cornea 10 and remaining portions of the eye upon implantation, including the anterior 11 and posterior 12 portions of the cornea 10, as well as the anterior chamber 13, iris 14, lens 15, vitreous humour 16, conjunctiva 17, and sclera 18.

While the anterior 26 and posterior 27 curvatures of the central region 22 may be collectively disposed to provide a net optically neutral transmission of light, that is, no vision correction, in some embodiments the central region 22 may comprise a vision correcting configuration, wherein the index of refraction of the central region 22 is sufficiently high to permit correction of refraction upon implantation. For instance, the central region 22 may be configured so that the anterior 26 and posterior curvatures 27 collectively create dioptric correction of a patient's vision, such as myopia or hyperopia, or even multifocal correction allowing for near and far vision, upon implantation of the corneal implant 20. Accordingly, the corneal implant 20 may comprise varying widths to accomplish the various types of vision correction. By way of example, the central region 22 may be thicker in the center than at the edges, or vice versa, and one edge could be of a different thickness than an opposite edge.

Looking further to FIGS. 1-3 and a preferred embodiment of the corneal implant 20, it also preferably includes at least one retention member 24 disposed along the periphery of the central region 22. The one, but preferably more than one retention members 24 are secured to and extending away from the central region 22. In this regard, the retention members may be integrally formed with the central region 22, such as of the same material, and/or may be separately formed and secured to the central region 22 as needed for proper fastening. Moreover, the retention member(s) 24 may be made of different material than the central region 22 of the corneal implant 20. For instance, the retention member(s) 24 may be made of a softer or more flexible material than the central region 22, or alternatively may be less flexible than the central region 22, and need not be transparent. Also, the retention member(s) 24 may comprise a hydrophilic material so as to be more compatible with the tissue of the eye which they contact and/or engage. In the illustrated embodiment, each retention member 24 has a width of approximately 0.5-5 micrometers, although it is contemplated that that width may vary, and indeed, in at least one embodiment, the retention members can measure 1-2 micrometers wide.

Each retention member 24 is structured and disposed to removably retain the corneal implant 20, and more in particular the central region 22 thereof in position relative to the posterior cornea upon implantation, maintaining placement but nevertheless permitting removal of the corneal implant 20, if necessary. For instance, as will be described in greater detail subsequently and as best seen in FIGS. 2A and 2B, the retention member(s) 24 may comprise a hook or claw type structure 28 or other suitable structure that enables stable and yet removable retention of the corneal implant 20 in attached relation to the eye.

Figure 2A:
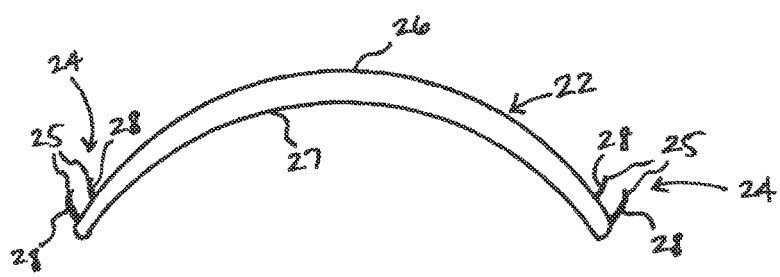
FIG. 2A is a side view of one embodiment of the corneal implant of FIG. 1.
Figure 2B:
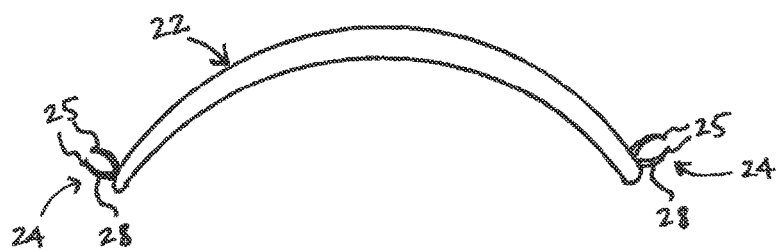
FIG. 2B is a side view of another embodiment of the corneal implant of FIG. 1.
Figure 3:
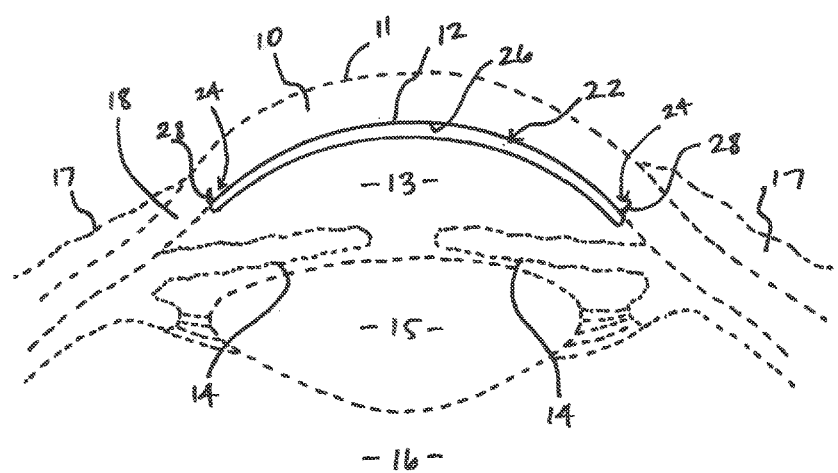
FIG. 3 is a side view of the corneal implant of FIG. 1 upon implantation and in position relative to the eye, shown in cross-section.

To facilitate engagement and securing of the corneal implant 20 to the eye, the retention member(s) 24 each preferably include a contact point 25 disposed distally from the central region 22 of the corneal implant 20, as seen in FIGS. 1, 2A, and 2B. The contact points 25 are disposed in contacting relation with an eye of the patient upon implantation, so as to retain the corneal implant 20 in abutting engagement relative to the posterior cornea 12, and may act as the point of at least initial engagement for each retention member 24 upon securing to the posterior cornea 12. For example, in at least one embodiment the retention members 24 can be pressed into the posterior cornea 12 such that the contact point 25 is the piercing point which first enters the corneal stroma leading the way for at least partial implantation of a remainder of the retention member 24 into the eye.

Figure 4:
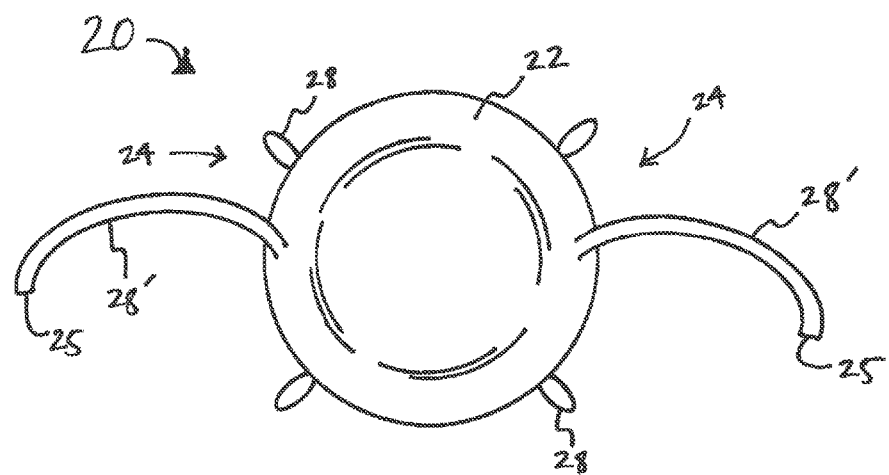
FIG. 4 is a planar view of the posterior side of another embodiment of the corneal implant of the present invention including haptic legs.
Figure 5:
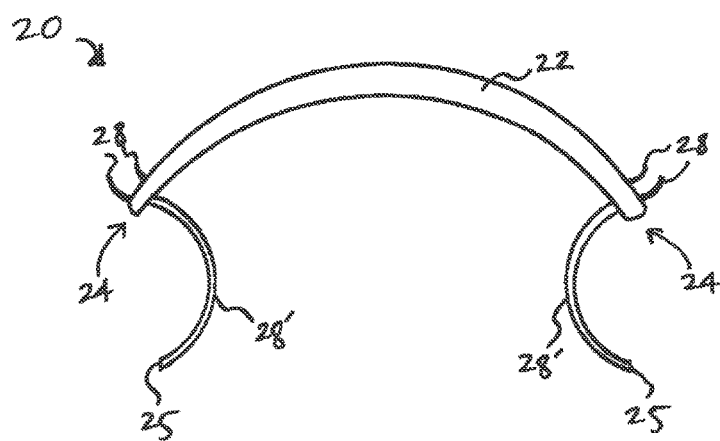
FIG. 5 is a side view of one embodiment of the corneal implant of FIG. 4.
Figure 6:
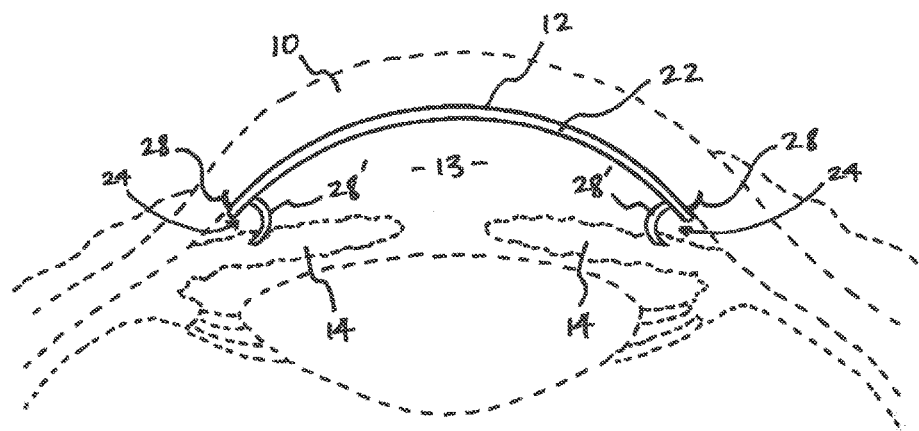
FIG. 6 is a side view of the corneal implant of FIG. 4 upon implantation and in one position relative to the eye, shown in cross-section, wherein the haptic legs contact the iris.
Figure 7:
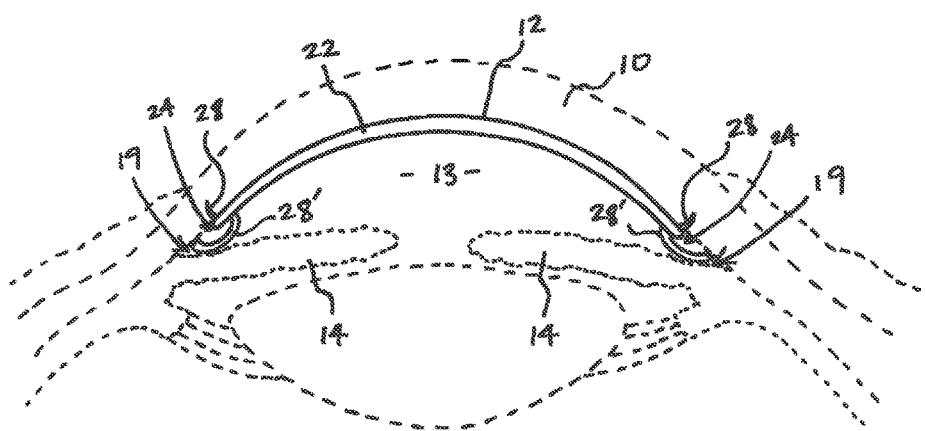
FIG. 7 is a side view of the corneal implant of FIG. 4 upon implantation and in another position relative to the eye, shown in cross-section, wherein the haptic legs contact the iridocorneal angle.

Looking further to the preferred corneal implant 20, and as shown in FIGS. 4-7, in at least one embodiment the retention members 24 can include at least one, but preferably two to four haptic legs 28' disposed either instead of or in addition to the other configurations of retention members 24, such as the hook or claw type configuration 28. Accordingly, some embodiments of the corneal implant 20 will have only hook or claw type retention member(s) 28, some embodiments only haptic leg(s) 28', and some embodiments will include a combination of hook or claw type retention member(s) 28 and haptic leg(s) 28'. With particular reference to FIGS. 4 and 5 wherein the haptic legs 28' are included as a retention member 24 in addition to other types of retention members 28, the haptic leg(s) 28' are secured to and extend away from the central region 22 of the corneal implant 20 such that a combined diameter of the central region 22 and haptic leg(s) 28' may be in the range of about 12-16 millimeters, and may preferably be in the range of about 13-14 millimeters. Each haptic leg 28' ends in a contact point 25 disposed distally from the central region 22, similar to the other types of retention member(s) 28. The haptic legs 28', however, have a biased configuration which is structured to bias, or push, the central region 22 against the posterior cornea 12 upon implantation, as depicted in FIGS. 6 and 7. For example, the haptic legs 28' are structured to provide sufficient pressure on the central portion 22 to maintain the position of the corneal implant 20 in engaging and abutting relation to the posterior cornea 12. The pressure applied by the haptic legs 28' and the central region 22 against the posterior cornea 12 depends on the particular configuration and disposition of the haptic leg 28', the material from which it is made, the tension or potential energy created by positioning the haptic leg 28', as well as other factors, but is nevertheless greater than intraocular pressure. For example, the haptic leg(s) 28' may apply anywhere from 15 35 mmHg of pressure on the central region 22, and consequently, the posterior cornea 12. In one preferred embodiment, the pressure applied by the haptic legs 28' is in the range of about 22-26 mmHg. Accordingly, and as seen in the embodiments of FIGS. 4-7, the biasing structure of the haptic legs 28' may comprise a curved, almost spring-like shape in order to create sufficient pressure of the corneal implant 20 on the posterior cornea 12. In some embodiments the haptic leg(s) 28' may be hinged to increase or decrease pressure applied to the central region 22.

As best shown in FIGS. 6 and 7, the haptic leg(s) 28' may be structured to span at least a portion of the anterior chamber 13 of the eye in order to bias the corneal implant 20 off neighboring portions of the eye. For example, the haptic legs 28' are structured and disposed so that the contact points 25 thereof releaseably engage a portion of the iris 14, as in FIG. 6, or the iridocorneal angle 19, as in FIG. 7. Accordingly, the haptic legs 28' push off of the iris 14 or iridocorneal angle 19, respectively, by virtue of the biasing configuration, to create the pressure on the central region 22, and thereby the posterior cornea 12, to maintain placement of the corneal implant 20. It should therefore be appreciated that the haptic legs 28' may comprise any material of sufficient strength, flexibility and resilience to create such a biasing effect. For example, the haptic leg(s) 28' may be made of a material that is harder or softer, and may be more or less flexible or pliable, than that of the central region 22 in order to achieve a particular desired pressure on the corneal implant 20 against the posterior cornea 12. The haptic leg(s) 28' may also comprise a hydrophilic material so as to be more compatible with the tissue of the eye which they contact and/or engage.

Taking into account these described, preferred embodiments of the corneal implant, and as noted, the present invention is also preferably directed to a method of inserting a corneal implant 20 in a manner that it is, in the preferred embodiments removably positioned relative to the posterior cornea, thereby allowing for removal and if needed interchanging of the corneal implant.

While it is noted that the each of the to be described embodiments of the present method, including the second embodiment where in the corneal implant is inserted into the corneal stroma, may also be removable, the removability is preferably achieved as will be described in connection with the first embodiment of the present method illustrated in FIG. 8.

Specifically, as noted, the present invention is directed to a method of inserting a corneal implant, which in the first preferred embodiment, as at 300, may optimally utilize the preferred corneal implant including one or more retention members. Moreover, looking in detail to the method, the initial steps will be described in connection with said first preferred embodiment for ease of explanation, although it is noted that many of the initial steps will apply to the other embodiments as well. In particular, once the eye is prepared for the procedure, the method, such as at 300, comprises an initial step of creating an incision in the eye in proximity to the cornea, as at 310. In many embodiments, the incision is made in the cornea itself, although it is understood that the incision may be made in other parts of the eye, such as the sclera, conjunctiva, etc. The incision is ideally of a relative small size to minimize damage and stress to the eye, such as in the range of about 1.8 to 3.0 millimeters. However, larger incisions of up to about 6 millimeters are contemplated. The incision permits access to the interior of the eye, such as to the anterior chamber and posterior surface of the cornea, against which the corneal implant will attach or be pressed. Alternately, however, the term incision also contemplates a much broader cut, such as what may be desired to create a corneal flap. It is understood that this incision can be made by manual, mechanical, or laser-based means as needed for precision.

Once the incision is made, the method, as at 300, also comprises inserting a corneal implant into the cornea through the incision, as at 320. Any corneal implant can be used in the present method, such as described above, including transplant tissue, although the preferred corneal implant described subsequently is preferred. In particular, the preferred corneal implant is preferably structured of a sufficiently thin dimension and resilient material to be foldable or at least temporarily compressible, such that inserting the corneal implant is achieved by compressing the corneal implant to a dimension smaller than the size of the incision, and then fitting the corneal implant through the smaller incision. Of course, it is understood that larger incisions may be needed, however, for inserting corneal implants that are more rigid and not foldable, or wherein a folding or compressing of the implant may be adverse to its ultimate function, such larger incisions and/or more rigid implants also contemplated by the present invention.

In the preferred embodiments, the corneal implant is inserted into the anterior chamber, posterior cornea, or other part of the eye which affords the corneal implant access to the posterior cornea, or at least the posterior surface of the cornea. As such, once the corneal implant is inserted through the incision, the method, such as at 300, further comprises positioning the corneal implant in engaging and fluid-flow limiting relation to the posterior cornea, as at 330. Specifically, as noted, the corneal implant is preferably made of a material that resists and/or limits the flow of aqueous fluid therethrough, such as a hydrophobic material. In some preferred embodiments, the material can include, although is not limited to, poly(2-hydroxyethylmethacrylate-co-methylmethacrylate) (pHEMA-MMA) and poly(2-hydroxyethyl methacrylate-co-ethylmethacrylate) (pHEMA-EMA), and which has a water content in the range of about 10-50%. Accordingly, the corneal implant, when positioned in contacting and engaging relation with the posterior cornea, effectively restricts the influx of fluid from the anterior chamber of the eye into the cornea by way of the corneal endothelium located along the posterior surface of the cornea, thereby reducing excess accumulation of fluid within the cornea. Of course, the corneal implant need not entirely prohibit all fluid flow, as complete blockage of fluid flow would, in fact, be detrimental to eye health since some transfer of anterior fluid is needed to provide nutrients to the cornea from the body. Instead, the corneal implant is structured and positioned so as limit the excessive influx of fluid from the anterior chamber into the cornea that causes edema, thereby restricting unwanted and painful fluid accumulation. Therefore, the corneal implant is positioned where it can be most effective at limiting influx of anterior fluid, and is preferably secured in place as will be described subsequently in a manner that while it presses against the posterior surface of the cornea, is preferably not completely secured thereto along the entire contacting surface.

Figure 8:
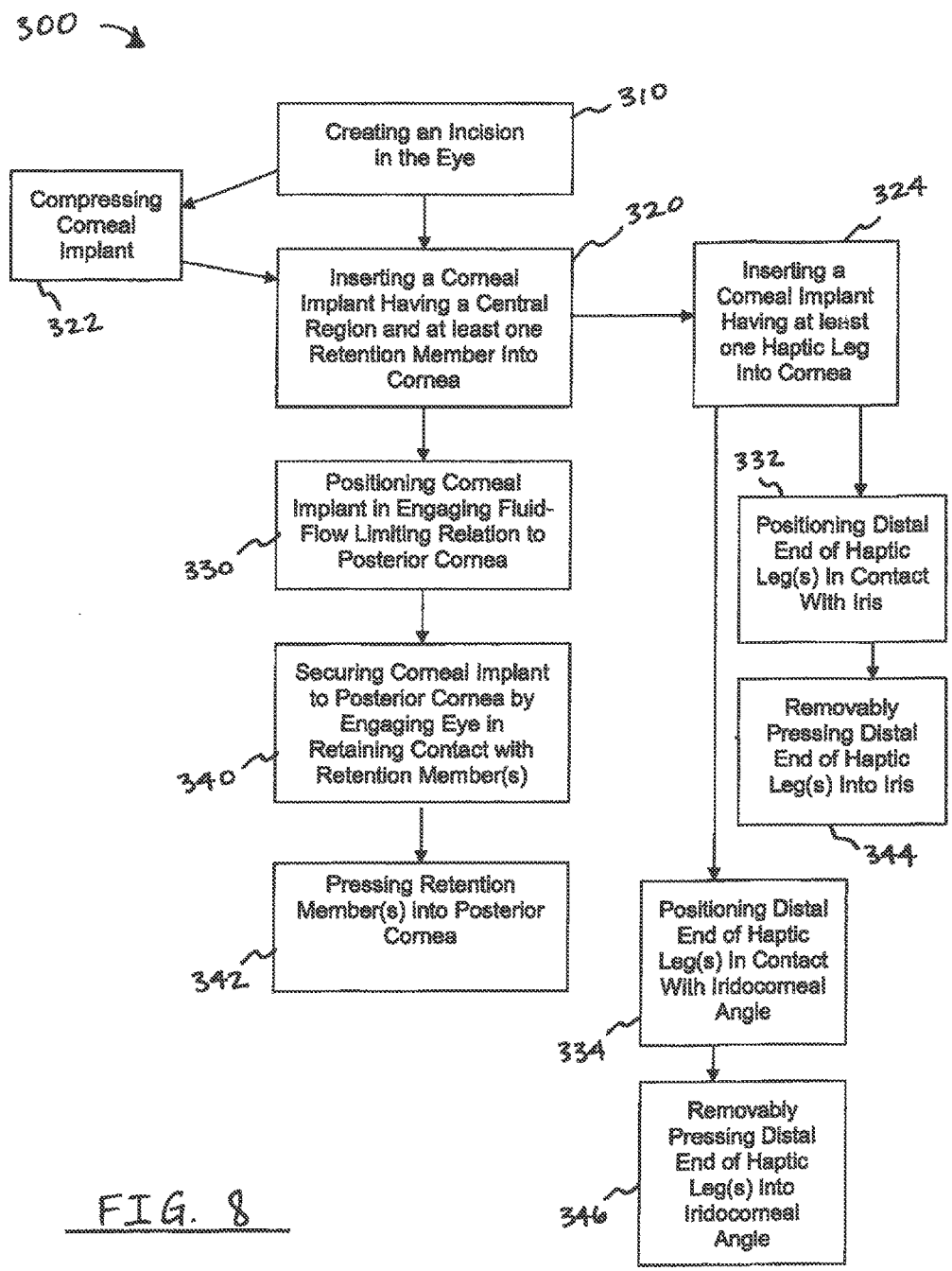
FIG. 8 is a schematic diagram of one embodiment of the present method whereby the corneal implant is secured by at least one retention member.

Specifically, and with reference to FIG. 8, the method, as at 300, can comprise inserting a corneal implant having at least one, but preferably a plurality of retention members into the eye. In this regard, FIG. 3 illustrates the proper positioning of the corneal implant 20, and in particular the central region 22, relative to the cornea 10 and other components of the eye in this and other embodiments of the present method. As previously noted, the corneal implant 20 is structured and positioned to limit the flow of anterior fluid into the cornea 10, such as by the corneal endothelium at the posterior cornea 12. Accordingly, the corneal implant 20 is positioned so as to engage the posterior cornea 12, such as by abutting or confronting relation thereto. As also mentioned above, the anterior curvature 26 of the central region 22 of the corneal implant 20 is configured to correspond with the posterior cornea 12 in order to facilitate and maximize abutting engagement with the posterior cornea 12.

Once positioned, the method, as at 300, further comprises securing the corneal implant in engaging and fluid-flow limiting relation to the posterior cornea by engaging portions of the eye in retaining contact with the retention member(s), as at 340, as shown in FIG. 8. Further, depending on the particular construction of the retention member(s), the eye may be engaged in different ways. For example, in one embodiment, securing the corneal implant occurs by pressing the retention member(s) into the posterior cornea, as at 342, so as to removably retain the corneal implant in position in relation thereto. In such an embodiment the retention member(s) 24 is structured so as to hook, grasp, latch onto, or otherwise engage a portion of the eye, such as the posterior cornea as shown in FIG. 3, in order to be retained thereby, while also allowing for removal of the corneal implant if necessary merely by disengaging the retention members 24 from within the eye.

When a corneal implant 20 includes at least one haptic leg 28', as described, the method of inserting the corneal implant, as at 300, can include positioning the distal end of the haptic leg(s) 28' in contacting relation to the iris and in biasing relation to the central region of the corneal implant against the posterior cornea, as at 332, and as shown in FIG. 8. In other cases, the distal end of the haptic leg(s) may be positioned in contacting relation to the iridocorneal angle, as at 334. Furthermore, in some embodiments the placement and biasing configuration of the haptic leg(s) may be sufficient to maintain positioning of the corneal implant against the posterior cornea with only contacting engagement of the distal end of the haptic leg(s) with the iris and/or iridocorneal angle. In other embodiments, however, it may be beneficial or desirable to secure the haptic leg(s) to the iris and/or iridocorneal angle, respectively, such as by penetration or other fastening or to include additional retention members to engage the eye, to maintain stable positioning of the central region of the corneal implant against the posterior cornea. Accordingly, the method may further comprise securing the corneal implant to the posterior cornea by removably pressing the distal end of the haptic leg into the iris, as at 344, or into the iridocorneal angle, as at 346, depending on where the haptic leg(s) is positioned to contact.

Finally, upon achieving proper positioning of the corneal implant, the method as at 300 comprises closing the incision in the cornea. For example, closing the incision may occur by replacing a flap created by the incision or delamination to its original location, whereupon the incision will close by the natural healing process of the eye.

In a further embodiment of the present method of inserting a corneal implant of the present invention, as at 200, the corneal implant is inserted into the corneal stroma of the eye, and may be secured within a pocket created in the cornea. This embodiment of the present method, as at 200, provides the benefit of being able to insert a corneal implant into the corneal stroma while avoiding entering the anterior chamber of the eye, and thus avoiding potential endoocular infections, such as endophalmitis, that can result. Moreover, this method, as at 200, is a simple surgical procedure that any ophthalmic surgeon can perform.

Figure 9:
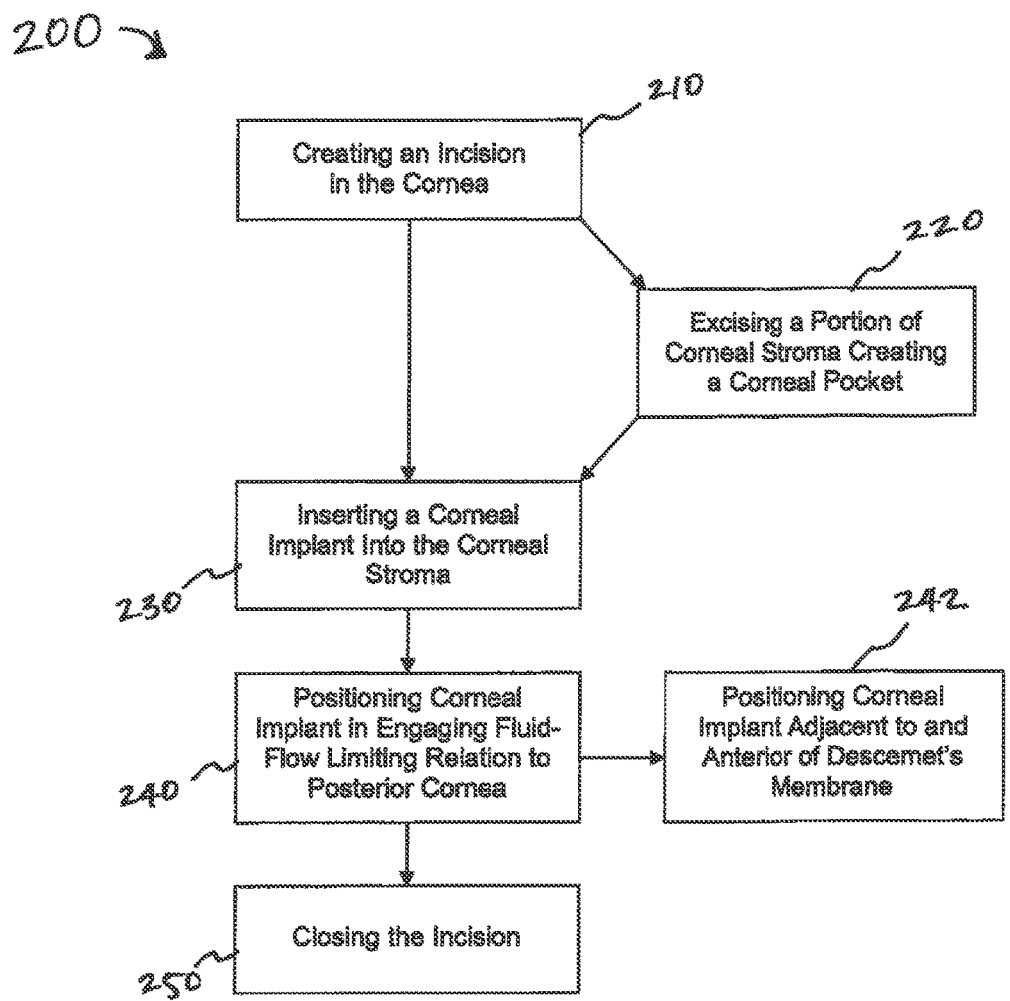
FIG. 9 is a schematic diagram of one embodiment of the present method whereby the corneal implant is secured in a corneal pocket.

As seen in FIG. 9, the method as at 200 comprises creating an incision in the cornea of the eye, as at 210, although the incision may be made in other parts of the eye in proximity to the cornea, such as the sclera, so as to expose at least a portion of the corneal stroma. Preferably, the incision is made in the superficial layer of cornea, such as the surface, and as before, the incision can be a small incision in the range of about 1.8 to 3.0 millimeters for inserting foldable corneal implants, or can be larger such as approximately 6 millimeters to accommodate rigid corneal implants. Accordingly, the incision may be used to delaminate a plane of the cornea in a particular location to enable access to the corneal stroma. In some examples, the incision may be configured to create a flap of tissue in which at least one portion is disconnected from the surrounding tissue but another side remains intact. The flap may be pulled to one side, such as moving the detached edge about the retained edge, and held in such orientation for the remainder of the implant insertion process. Moreover, the incision can be created manually (such as with a blade or razor), mechanically (such as with a microkeratome or other device), or laser-assisted (such as with a femtosecond laser).

Figure 10:
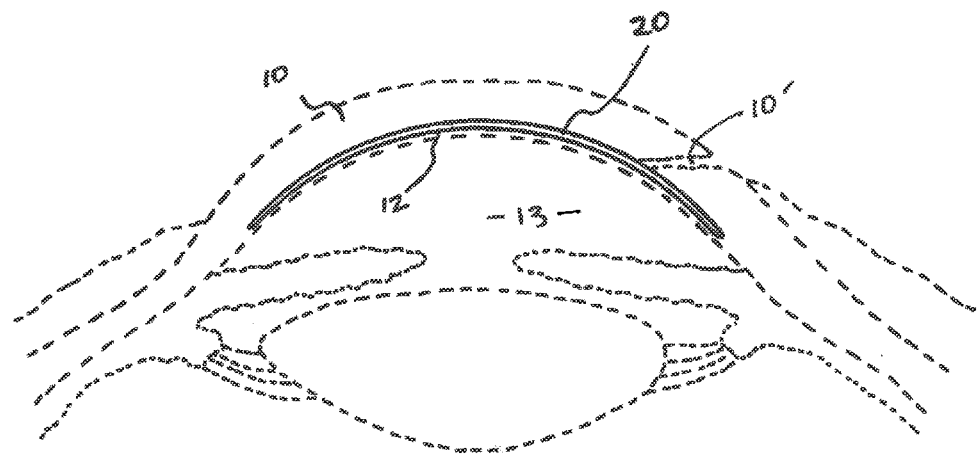
FIG. 10 is a side view of the corneal implant upon corneal insertion by the method of FIG. 9, shown in cross-section.

The embodiment of the present method, as at 200, may further comprise excising a portion of cornea from the eye through the incision, thereby creating a corneal pocket, as at 220. The amount, dimension, shape, and location of cornea excised or removed from the eye may vary depending on the size of the corneal implant or as determined to be appropriate by a surgeon, ophthalmologist, or corneal specialist. For example, excising a portion of cornea may entail excising a portion of deep cornea, thereby creating a deep corneal stromal pocket, and may be excised from the side of the cornea, as shown in FIG. 10 by the pocket 10'. Moreover, excision comprises removing a portion of corneal stroma that is at least as large in size and configuration as the corneal implant intended for implantation. In some embodiments, the pocket is larger than the corneal implant to enable the implant to be fully enclosed in the resulting pocket upon implantation. In other examples, the pocket may be smaller than the full size of the corneal implant, but is sufficiently sized and located to permit access to the corneal stroma, whereby the corneal implant extends from the pocket into the neighboring corneal stroma, such as is depicted in FIG. 10.

With reference to FIG. 9, the method as at 200 further comprises inserting the corneal implant into the corneal stroma, as at 230. This may be accomplished through the incision, and when a corneal pocket is made, through the corneal pocket. It should be understood, however, that the creation of and insertion through a corneal pocket is not required for this embodiment of the method 200, and in some cases an incision is all that is necessary to access the corneal stroma. For example, if the corneal implant is very thin, such as having a thickness ranging from about 10 micrometers to 125 micrometers, the corneal implant may be inserted directly into the corneal stroma without prior tissue excision. Indeed, the incision in the cornea creates access to the corneal stroma, into which the implant may be inserted, even in the absence of tissue excision.

The corneal implant inserted by method 200 can be any implant, natural or synthetic as described previously, but is preferably made of clear transparent biocompatible material of medical grade quality, and preferably does not contain any form of retention member(s), although in some embodiments retention members can be present for added securing upon placement. The implant may also preferably be made of semi-rigid yet foldable material. Accordingly, insertion of the implant may include compressing the corneal implant to a dimension smaller than the size of the incision in the cornea as previously recited, and the opening of the corneal pocket in cases where a pocket is created, for insertion therethrough. Once inside the corneal stroma or pocket, compression on the corneal implant is released, permitting the implant to assume its natural configuration within the stroma or pocket. However, it is also contemplated that corneal implant may not be foldable, and therefore is simply inserted through a larger incision and into the corneal pocket in its native configuration.

Once inserted into the corneal stroma, the method, as at 200, further comprises positioning the corneal implant within the stroma in engaging and fluid-flow limiting relation to the posterior cornea, as at 240. As described previously, the corneal implant is positioned so as to limit flow of anterior fluid into the cornea through the posterior endothelium, such as to dehydrate the cornea from an edematous state to a normal level, and to maintain a normal level of corneal fluid once obtained by preventing further excess anterior fluid from entering the cornea. In one example, proper positioning of the corneal implant includes positioning the corneal implant within the corneal stroma adjacent to and anterior of the Descemet's membrane, as at 242. For instance, the corneal implant may be inserted through the corneal pocket and into the corneal stroma to be positioned adjacent to the Descemet's membrane. Of course, it should be appreciated that positioning the corneal implant, as at 240, may entail positioning the corneal implant anywhere in the corneal pocket and/or cornea that will limit the flow of fluid into the cornea, such as by the posterior cornea.

Figure 11:
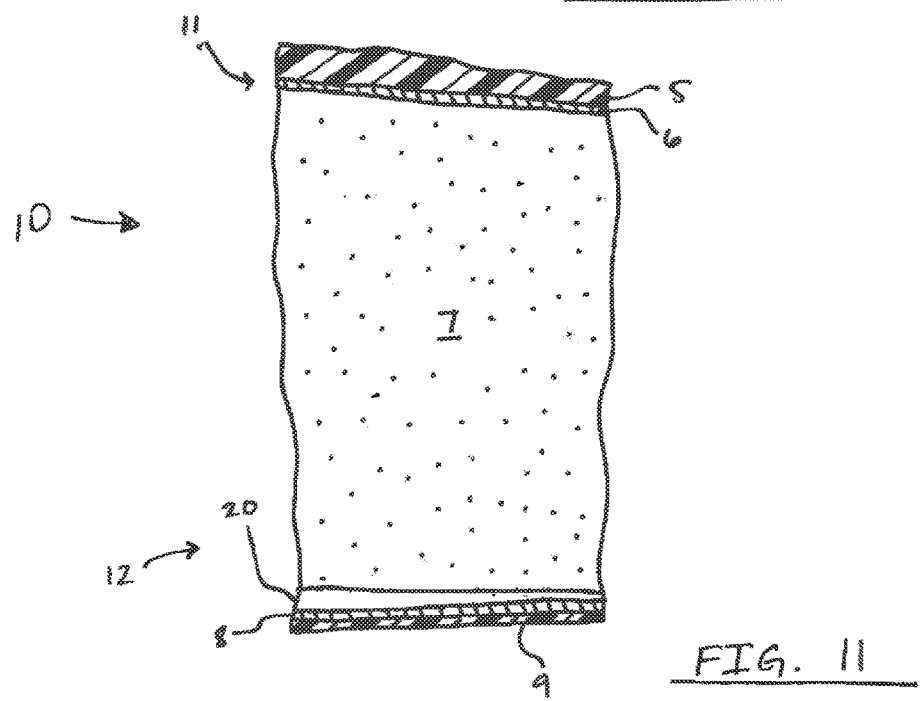
FIG. 11 is a close-up side view in cross-section of the placement of the corneal insert in relation to the layers of the cornea.

FIGS. 10 and 11 illustrate examples of proper positioning of the corneal implant 22 in relation to the cornea 10 as inserted in accordance with method 200. For example, FIG. 10 shows the corneal implant 20 positioned within the posterior cornea 12, having been inserted through a corneal pocket 10', thus avoiding entering the anterior chamber 13. FIG. 11 shows a cross-section of the cornea depicting one preferred placement for the corneal implant 20 within the layers of the cornea 10. For instance, the corneal implant 20 is positioned near the posterior 12 side of the cornea, just anterior to the natural Descemet's membrane 8. The corneal epithelium 5, anterior elastic lamina 6, stroma 7, and endothelium 9 are also shown for illustrative purposes.

In a preferred embodiment, the proper positioning of the corneal implant is maintained by virtue of the fit of the corneal implant within the corneal pocket and/or corneal stroma, which is sufficiently tight to keep the corneal implant from moving out of place, particularly when the corneal implant is inserted or 'wedged' into the corneal stroma without the use of a corneal pocket. However, additional structure may be included on the corneal implant, such as in the form of retention members, to provide attachment points to retain the corneal implant in place for additional securement of the corneal implant in position.

Finally, upon achieving proper positioning of the corneal implant, the method as at 200 also comprises closing the incision in the cornea, as at 250, and as shown in FIG. 9. For example, as noted, closing the incision may occur by replacing a flap created by the incision or delamination to its original location, whereupon the incision will close by the natural healing process of the eye.

Figure 12:
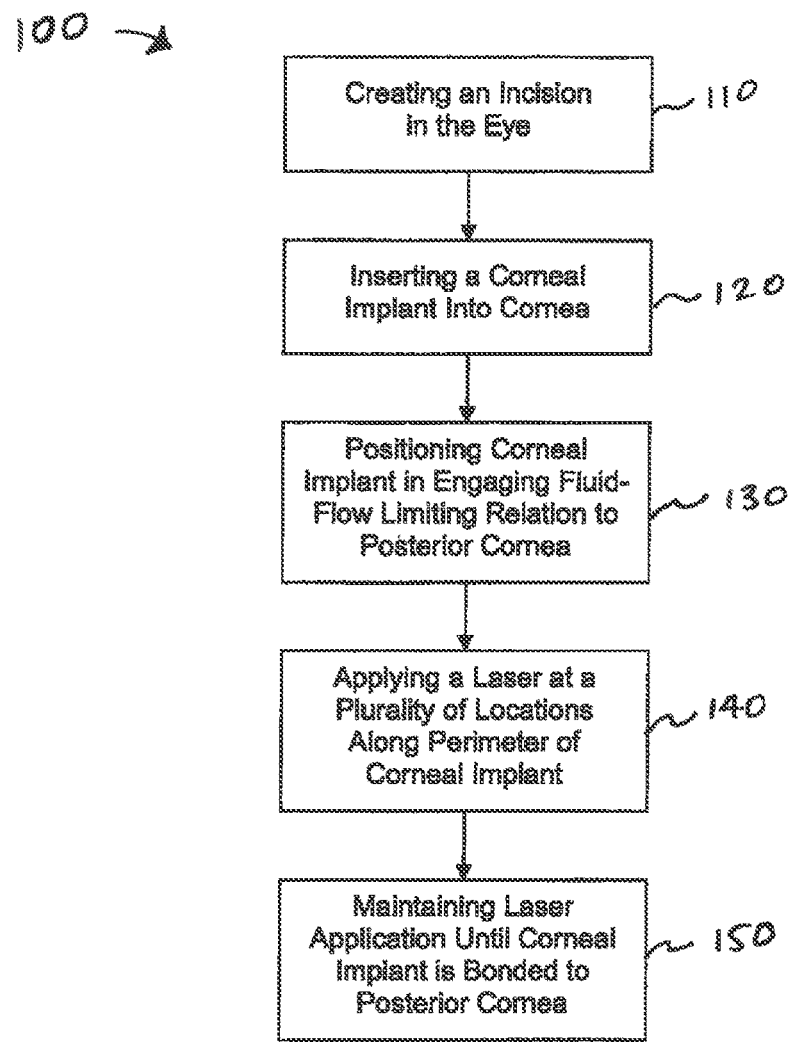
FIG. 12 is a schematic diagram of one embodiment of the present method whereby the corneal implant is secured by laser.

Looking now at yet another embodiment of the present method, as at 100, diagrammed in FIG. 12, once the corneal implant is inserted through the incisions and properly positioned relative to the posterior cornea, it is preferably bonded to the eye, such as using a laser. In particular, a laser is applied at a plurality of locations along a perimeter of the corneal implant, as at 140, after it has been positioned within the eye. Specifically, the present invention contemplates the use of any laser that provides matching or corresponding energy to the particular chromophore used to accomplish the laser bonding of the corneal implant to the posterior cornea.

Naturally, the type of laser employed will utilize specific wavelengths of light and provide different amounts of power or thermal energy as compared with other lasers, the objective preferably being to utilize a laser that can achieve effective bonding as will be described, with minimal impact on the eye and the patent. For example, the laser may be a solid state laser, such as a neodymium-doped yttrium aluminum garnet crystal (Nd:YAG) or ruby. Alternately, however, the laser may be a gas laser, such as comprising helium (He), nitrogen (N), argon (Ar), or carbon dioxide (C02) as the lasing medium. In further examples, the laser may be a fiber optic, or preferably, a diode or diode-pumped laser, and may be ultrafast, such as a femtosecond laser.

In particular, the step of applying the laser, as at 140, entails directing the laser to a desired focal point where the energy of the laser is concentrated. The focal point of the laser can include at the surface of the corneal implant, at a point within the posterior cornea, at the junction of the corneal implant with the posterior surface of the cornea, and/or at some other location sufficient to achieve excitation and an increase in thermal energy in the corneal implant as well as the corresponding posterior cornea. Moreover, the laser can be operated to provide continuous laser light, and therefore continuous energy, or can be applied in pulses or short bursts, such as to minimize trauma to the eye.

In this embodiment of the present method, as at 100, once applied, the laser application is maintained until the implant is bonded to the posterior cornea of the patient, as at 150. In this regard, the laser is preferably maintained at each location along a perimeter of the corneal implant where attachment is desired so as to bond the implant to the posterior cornea at that particular location. Bonding generally occurs when the light energy provided by the laser is converted to thermal energy and the corneal implant and abutting posterior cornea are heated until they coalesce, that is, until the corresponding portions of the implant and posterior cornea subject to the laser application melt together. Cessation of the laser application then initiates cooling of the melted portion, after which the corneal implant and posterior cornea are securely joined at that location.

Applying 140 and maintaining 150 the laser is performed until a plurality of locations of the corneal implant are bonded to the posterior cornea. This can occur at successive distinct locations along the corneal implant, moving to a new location once a previous location is securely bonded, although it is noted that continuous movement about the perimeter of the corneal implant so as to achieve complete securing about the perimeter such that uninterrupted lengths of the corneal implant are bonded to the posterior cornea, or to achieve larger than merely spot attachment points is also contemplated. Moreover, the number of locations of laser application and bonding may vary so long as there are at least a sufficient number of locations to secure the corneal implant to the posterior cornea in a particular position relative thereto. For instance, in some embodiments, a minimum of two or three properly spaced bonding locations is all that may be needed to secure the corneal implant in place. As noted, in some embodiments, however, the laser is applied and maintained along substantially the entire perimeter of the corneal implant, such that multiple points along the entire circumference of the corneal implant are bonded to the posterior cornea, however, this may be less preferred if some 'breathability' is desired. The length of such laser application may vary based on what is determined by the surgeon, corneal or other ophthalmologic professional performing the present method deems appropriate and/or necessary. For example, the laser can be applied and maintained to create essentially a dashed line along the perimeter of the corneal implant which bonds the implant to the posterior cornea. Of course, in all embodiments, the number of points will depend on the size and circumference of the corneal implant, as well as on the size of the focal point of the laser, the thermal energy created by the laser, and the size of resulting melted material that subsequently cools together. As with the other embodiments, once the corneal implant is effectively positioned and secured, the incisions may be closed or be permitted to close via natural healing.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A corneal implant for treating excess corneal fluid, said corneal implant comprising:
    a central region providing an anterior surface and a posterior surface, the anterior surface comprising a posterior-cornea-engaging surface, the posterior surface disposable in facing relation to the interior of the eye upon implantation, the central region made of a biocompatible material and configured to correspond to a contour of a posterior cornea,
    a plurality of retention members secured to and extending away from a periphery of said central region of said corneal implant and structured to removably retain said corneal implant in position in relation to the posterior cornea upon implantation, and each of said retention members including a hook or claw type structure having a contact point disposed distally from said central region corneal implant and in contacting relation with an eye of a patient, such that, upon implantation, said contact point is structured to retain said corneal implant in abutting engagement with the posterior cornea,
    wherein each of said retention members further includes at least one haptic leg secured to and extending away from said central region, said at least one haptic leg ending in a contact point disposed distally from the central region, said at least one haptic leg including a biased configuration structured to bias said central region against the posterior cornea,
    wherein said contact point of said hook or claw type structure is structured and disposed to releaseably engage a portion of the posterior cornea,
    wherein said contact point of said at least one haptic leg is structured and disposed to releaseably engage a portion of one of an iris or an iridocorneal angle,
    wherein said central region comprises an anterior curvature structured to at least partially conform to a curvature of the posterior cornea,
    wherein said at least one haptic leg is configured to exert pressure on said central region against the posterior cornea so as to maintain positioning of said central region upon implantation, and
    wherein said central region comprises a vision correcting configuration.

2. The corneal implant as recited in claim 1, wherein said central region comprises a hydrophobic material.

3. The corneal implant as recited in claim 1, wherein said central region is structured to inhibit the flow of excess corneal fluid.

4. The corneal implant as recited in claim 1, wherein said contact point of said haptic leg is structured and disposed to releaseably engage a portion of an iris.

5. The corneal implant as recited in claim 1, wherein said contact point of each of said haptic legs is structured and disposed to releaseably engage a portion of an iridocorneal angle.

6. The corneal implant as recited in claim 1, wherein the abutting engagement is configured to treat excess corneal fluid.

* * * * *